United States Patent
Hosoi et al.

(10) Patent No.: US 7,044,906 B2
(45) Date of Patent: May 16, 2006

(54) FLEXIBLE TUBE FOR AN ENDOSCOPE AND AN ENDOSCOPE EQUIPPED WITH THE FLEXIBLE TUBE

(75) Inventors: Masayoshi Hosoi, Tokyo (JP); Yoshihisa Shijo, Saitama (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 10/879,038

(22) Filed: Jun. 30, 2004

(65) Prior Publication Data

US 2005/0020882 A1   Jan. 27, 2005

(30) Foreign Application Priority Data

Jun. 30, 2003   (JP)   ............... 2003-188088

(51) Int. Cl.
*A61B 1/00*   (2006.01)
(52) U.S. Cl. ............... 600/139; 600/140; 600/141
(58) Field of Classification Search ............... 600/121, 600/133, 139, 140; 138/118, 140, 118.1, 138/137, DIG. 7
See application file for complete search history.

(56) References Cited

U.S. PATENT DOCUMENTS

| 4,616,064 | A |   | 10/1986 | Zukosky |   |
|---|---|---|---|---|---|
| 5,538,513 | A | * | 7/1996 | Okajima | ............... 604/527 |
| 6,458,075 | B1 | * | 10/2002 | Sugiyama et al. | ............ 600/139 |
| 6,520,214 | B1 |   | 2/2003 | Sugiyama et al. |   |
| 6,540,669 | B1 | * | 4/2003 | Abe et al. | ............... 600/140 |
| 6,599,239 | B1 |   | 7/2003 | Hayakawa et al. |   |
| 6,616,601 | B1 | * | 9/2003 | Hayakawa | ............... 600/140 |
| 6,623,424 | B1 |   | 9/2003 | Hayakawa |   |
| 2002/0010386 | A1 |   | 1/2002 | Matsushita et al. |   |
| 2002/0028984 | A1 |   | 3/2002 | Hayakawa et al. |   |
| 2002/0032368 | A1 |   | 3/2002 | Takase |   |
| 2002/0045802 | A1 |   | 4/2002 | Hascoet et al. |   |
| 2002/0143237 | A1 |   | 10/2002 | Oneda et al. |   |

FOREIGN PATENT DOCUMENTS

| EP | 1149598 | 10/2001 |
|---|---|---|
| EP | 1275891 | 1/2003 |
| JP | 7-110270 | 11/1995 |
| JP | 2001-161632 | 6/2001 |

* cited by examiner

*Primary Examiner*—Beverly M. Flanagan
(74) *Attorney, Agent, or Firm*—Greenblum & Bernstein, P.L.C.

(57) ABSTRACT

A flexible tube for an endoscope includes a tubular core member, and an outer cover provided around the core member, the outer cover being formed of a material containing as a major component thereof polyolefin-based thermoplastic elastomer and polyolefin, wherein the amount of the polyolefin contained in the material is 5 parts by weight with respect to 100 parts by weight of the polyolefin-based thermoplastic elastomer. The polyolefin is mainly constituted from polypropylene, and the average thickness of the outer cover is 0.08 to 0.9 mm.

14 Claims, 3 Drawing Sheets

FLEXIBLE TUBE FOR AN ENDOSCOPE AND AN ENDOSCOPE EQUIPPED WITH THE FLEXIBLE TUBE

BACKGROUND OF THE INVENTION

1. Field of the Invention

The present invention relates to a flexible tube for an endoscope and an endoscope equipped with the flexible tube.

2. Description of the Prior Art

In an endoscopic examination, a flexible insertion tube of an endoscope is inserted along the body cavity to a deep part of a patient such as the stomach, duodenum, small intestine, and large intestine. For this reason, the flexible insertion tube of the endoscope is provided with an outer cover to improve ease of the inserting operation (that is, flexibility), which reduces a burden on a patient. In addition, the outer cover prevents fluids such as body fluids from entering the interior of the endoscope. In the prior art, an elastic material such as urethane-based elastomer has been generally used as a constituent material of the outer cover of the flexible insertion tube (see Japanese Patent Publication No. Hei 7-110270 (page 1, right column, lines 2-8), for example).

In the meantime, since an endoscope is repeatedly used, it must be cleaned and disinfected after each use. However, the above-mentioned material which has been conventionally used has a problem in that heat resistance and chemical resistance thereof are poor. For this reason, repeated cleaning, sterilization and disinfection of the endoscope deteriorates the outer cover of the flexible insertion tube, and then the flexibility of the outer cover itself is lowered, which may result in a case that it becomes difficult to insert the flexible insertion tube into a tubular cavity. Further, in a case where such deterioration is severe, small cracks and the like will occur, and as a result, there is a case that the constituent material of the outer cover of the flexible insertion tube will peel off.

SUMMARY OF THE INVENTION

It is therefore an object of the present invention to provide a flexible tube for an endoscope having excellent heat resistance and chemical resistance with retaining adequate resilience, and an endoscope equipped with such a flexible tube.

In order to achieve the object, the present invention is directed to a flexible tube for an endoscope, comprising a tubular core member, and an outer cover provided around the core member, the outer cover being formed of a material containing as a major component thereof polyolefin-based thermoplastic elastomer and polyolefin, wherein the amount of the polyolefin contained in the material is 5 to 70 parts by weight with respect to 100 parts by weight of the polyolefin-based thermoplastic elastomer.

According to the present invention described above, it is possible to obtain a flexible tube for an endoscope having excellent chemical resistance and heat resistance with retaining adequate resilience.

In the present invention, it is preferred that the outer cover has a laminated structure including a plurality of layers, wherein at least one of the layers is formed of the material containing polyolefin-based thermoplastic elastomer and polyolefin.

In this case, it is preferred the layer formed of the material containing polyolefin-based thermoplastic elastomer and polyolefin is an outermost layer among the plurality of layers. Further, it is also preferred that the average thickness of the layer formed of the material containing polyolefin-based thermoplastic elastomer and polyolefin is in the range of 0.01 to 0.6 mm.

Further, in the present invention, it is preferred that the polyolefin is mainly constituted from polypropylene.

Furthermore, it is also preferred that the average thickness of the outer cover is in the range of 0.08 to 0.9 mm.

Another aspect of the present invention is directed to an endoscope equipped with the flexible tube as described in the above.

These and other objects, structures and results of the present invention will be apparent more clearly when the following detailed description of the preferred embodiments is considered taken in conjunction with the appended drawings.

DETAILED DESCRIPTION OF THE INVENTION

Hereinafter, a detailed description of the preferred embodiments of a flexible tube for an endoscope and an endoscope equipped with the flexible tube according to the present invention will be given with reference to the appended drawings.

Figure 1:
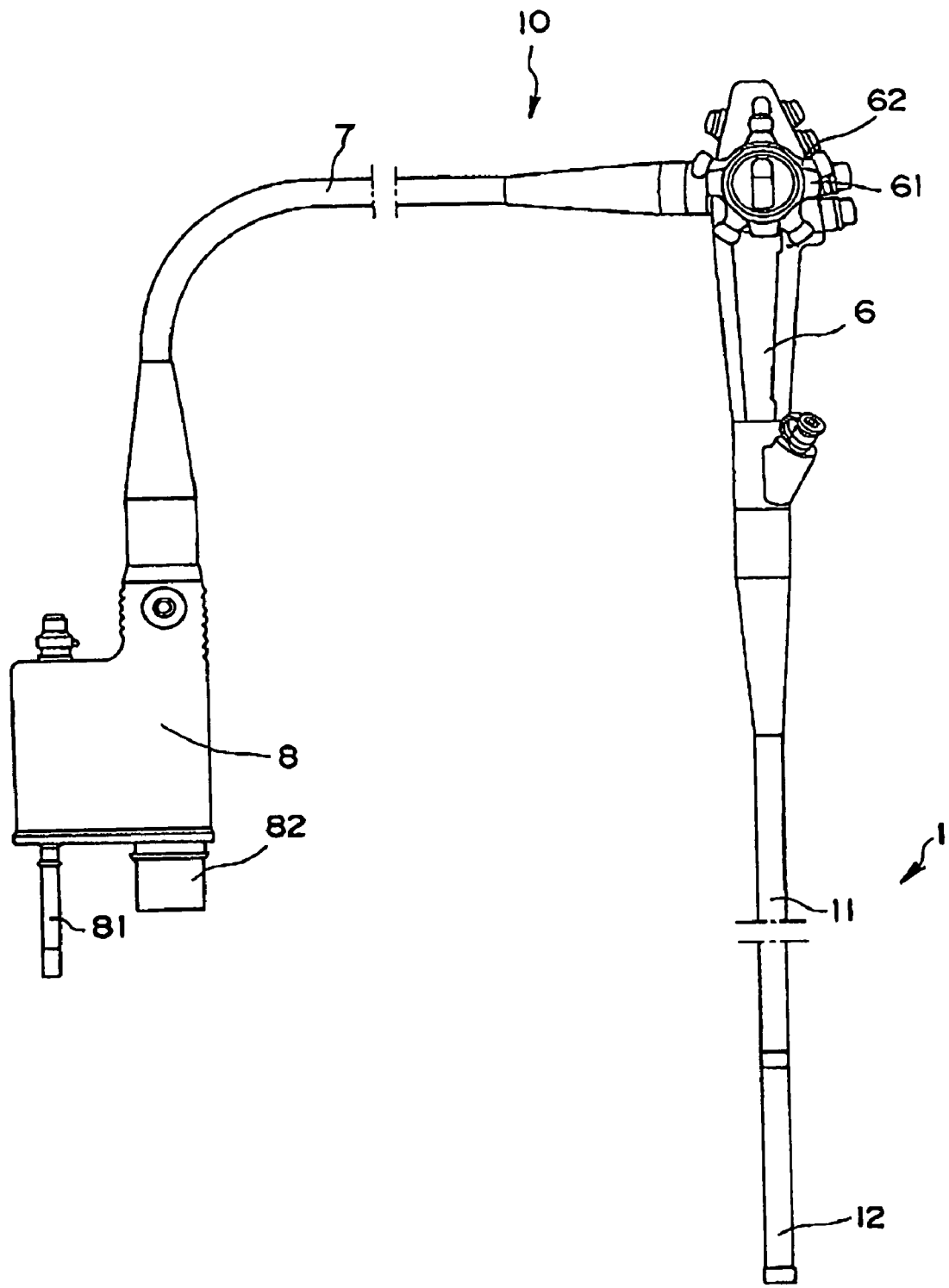
FIG. 1 is an overall view showing the embodiment of an electronic endoscope (electronic scope) to which the endoscope according to the present invention is applied.
Figure 2:
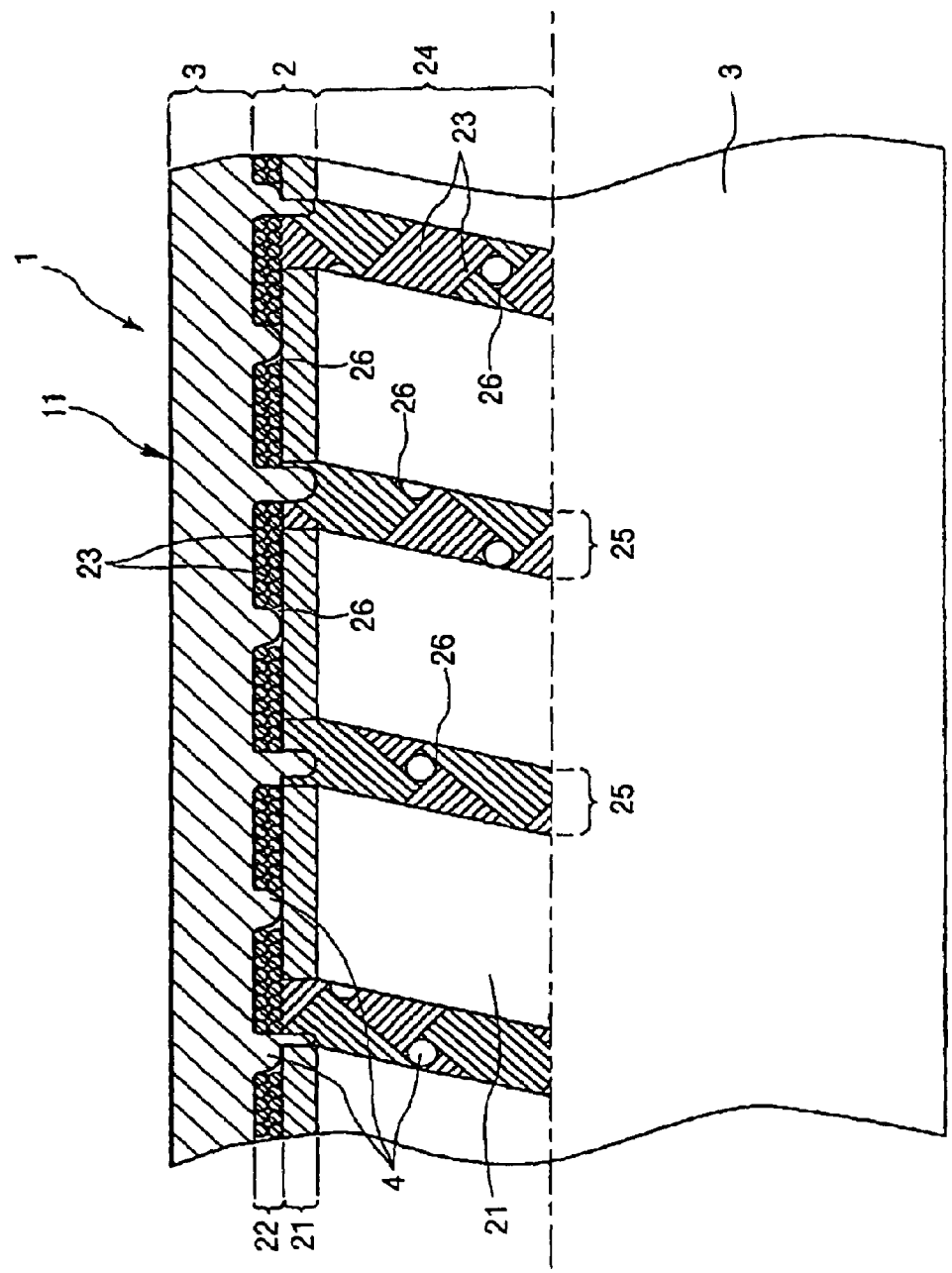
FIG. 2 is an enlarged longitudinal sectional view of a portion of a flexible tube of the electronic endoscope shown in FIG. 1.

FIG. 1 is an overall view showing the embodiment of an electronic endoscope (electronic scope) to which the endoscope according to the present invention is applied, and FIG. 2 is an enlarged longitudinal sectional view of a portion of a flexible tube of the electronic endoscope shown in FIG. 1. In the following description, the upper side and the lower side in FIG. 1 will be referred to as "base or proximal end" and "tip or distal end", respectively.

As shown in FIG. 1, an electronic endoscope 10 includes an elongated flexible insertion tube 1 having flexibility, an operating section 6 provided on the base end of the flexible insertion tube 1, which is held by an operator to manipulate the electronic endoscope 10, a flexible connection tube 7 connected at the one end thereof to the operating section 6, and a light source plug section 8 provided on the other end of the flexible connection tube 7. The flexible insertion tube 1 is constructed from a main flexible tube section 11 and a bendable tube section 12 provided at the tip of the main flexible tube section 11.

Each of the flexible insertion tube 1 and the flexible connection tube 7 is manufactured using a flexible tube for an endoscope of the present invention which is obtained by covering the outer periphery of a (tubular) core member having a hollow space with an outer cover 3.

On one side surface of the operating section 6, there are provided operating knobs 61 and 62. When changing the direction of the bendable tube section 12, the operator turns each of the operating knobs 61 and 62 to pull appropriately wires (not shown) arranged inside the flexible insertion tube 1. In this way, the bendable tube section 12 can be bent to a desired direction.

An imaging element (CCD) not shown in the drawings is provided inside the tip end portion of the bendable tube portion 12 to take observation images of an observation region. Further, an image signal connector 82 is provided at the tip end portion of the light source plug section 8. The image signal connector 82 is connected to a light source processor (not shown in the drawings) which is connected to a monitor (not shown In the drawings) via a cable. Furthermore, a light source connector 81 is provided at the tip end portion of the light source plug section 8, and this light source connector 81 is connected to the light source processor.

Light emitted from the light source processor passes through the light source connector 81 and a light guide (not shown in the drawings) that runs inside the light source plug section 8, the flexible connection tube 7, the operating section 6, and the flexible insertion tube 1, and then the light is irradiated from the tip end portion of the bendable tube section 12 (that is, the tip end of the flexible insertion tube 1) toward the observation region for illumination. Such a light guide is composed of a bundle of optical fibers made of quartz, multicomponent glass, plastic or the like, for example.

The reflected light from the observation region illuminated by the illumination light (observation image) is received by the imaging element. Then, the imaging element outputs an image signal corresponding to the observation image taken by the imaging element. The image signal is transmitted to the light source plug section 8 via an image signal cable (not shown in the drawings) which extends inside the flexible insertion tube 1, the operating section 6, and the flexible connection tube 7 in order to connect the imaging element and the image signal connector 82.

Then, in the light source plug section 8 and the light source processor, the image signal is subjected to predetermined processing (such as signal processing, image processing, and the like), and then the processed signal is sent to the monitor. In this way, an image (electronic image) taken by the imaging element is displayed on the screen of the monitor in the form of a motion picture.

<Flexible Insertion Tube 1>

As shown in FIG. 2, the flexible insertion tube 1 is constructed from the main flexible tube section 11 and the bendable tube section 12 provided at the tip of the main flexible tube section 11. The flexible insertion tube 1 has a core member 2 and the outer cover 3 that covers the outer periphery of the core member 2 (that is, the outer cover 3 is provided around the core member 2). Inside the flexible insertion tube 1 (that is, inside the core member 2), there are provided hollow spaces 24 through which elongated members such as optical fibers, electrical cables, wires, tubes and the like (which are omitted from the drawing) can be passed.

The core member 2 for the main flexible tube section 11 is constructed from a spiral coil 21 and a reticular tube (braided member) 22 which covers the outer periphery of the spiral coil 21. Further, the core member 2 for the bendable tube section 12 is constructed from a plurality of nodal rings (not shown in the drawings) rotatably coupled with each other and a reticular tube which covers the outer periphery of the nodal rings. In this way, the core member 2 is formed into an elongated tubular shape.

The spiral coil 21 is formed by winding a band-shaped member in a helical or spiral form with a gap 25 between the adjacent windings. Further, the spiral coil 21 is formed so as to have a substantially uniform internal diameter along the entire length thereof. Preferred examples of a material to be used for the spiral coil 21 and the nodal ring include stainless steel, copper alloys, and the like.

The reticular tube (such as the reticular tube 22) is formed by braiding a plurality of fine wire bundles in which each bundle includes metal or nonmetal fine wires 23 arranged side by side. Preferred examples of a material to be used for the fine wire 23 include stainless steel, copper alloys, and the like. Further, at least one of the fine wires 23 constituting the reticular tube may be covered with a resin material.

The reticular tube 22 has spaces (openings) 26 due to the stitches of the braided fine wires 23. These spaces 26 form concave portions at the positions that overlap with the outer periphery of the spiral coil 21, and form holes extending to the hollow spaces 24 at the positions that overlap with the gaps 25 of the spiral coil 21. Therefore, a plurality of holes and concave portions are formed in the outer periphery of the core member 2.

In the interior space of the core member 2 (that is, inside the flexible insertion tube 1), a solid lubricant such as molybdenum disulfide, boron nitride (BN), polytetrafluoroethylene (fluorine-based resin), graphite or fluorocarbon $((CF)_n)$ is provided. The solid lubricant is provided around the elongated members described above. This makes it possible to decrease sliding resistance (frictional resistance) between the elongated members or between each of the elongated members and the core member 2. Therefore, when the flexible insertion tube 1 (the main flexible tube section 11 and the bendable tube section 12) is bent, each of the elongated members smoothly moves in the longitudinal direction (axis direction) of the core member 2, so that the bending resistance thereof becomes small. Further, tension or pressure on the optical fibers constituting the light guide, or buckling of these optical fibers is suppressed, and as a result, damage or fracture of the light guide can be effectively prevented.

The outer periphery of the core member 2 is covered with the outer cover 3. The outer cover 3 has the function of preventing body fluids or the like from entering the interior of the flexible insertion tube 1, because the outer cover 3 directly comes into contact with the inner wall of a tubular organ such as the alimentary canal.

A plurality of protruding portions (anchors) 4 are integrally formed on the inner surface of the outer cover 3.

These protruding portions protrude toward the inside so as to extend into the spaces formed in the outer periphery of the core member 2. Specifically, these protruding portions 4 extend into the plurality of holes and concave portions formed in the outer periphery of the core member 2. The tips of the protruding portions 4 that protrude into the concave portions are formed so as to reach the outer periphery of the spiral coil 21. The protruding portions 4 that protrude into the holes are formed to be even longer so that the tips thereof can be extended into the gaps 25 of the spiral coil 21.

By forming these protruding portions 4, an anchoring effect can be obtained, and this provides reliable securing between the outer cover 3 and the core member 2. As a result, even in a case where the flexible insertion tube 1 is bent, the outer cover 3 will maintain an adhering state with the core member 2, and will undergo large expansion and contraction to follow the bending of the core member 2. Further, the restoring force of the outer cover 3 undergoing such large expansion and contraction is strong enough to serve as a force for restoring the shape of the bent flexible insertion tube 1.

Further, due to the protruding portions 4 described above, the outer cover 3 firmly adheres to the reticular tube 22, so that the outer cover 3 will be difficult to peel off from the reticular tube 22 even over repeated use. Accordingly, the flexible insertion tube 1 will have excellent durability.

In a case where at least one of the fine wires 23 constituting the reticular tube 22 is covered with a resin material, at least a part of the resin material (covering layer) is melted to be bonded (welded) to the outer cover 3.

Since such an outer cover 3 is exposed to chemicals such as various kinds of disinfectants or high temperatures and pressures during repeated disinfection or sterilization treatments, it is required for the outer cover 3 to have chemical resistance and heat resistance. In addition, it is also required that the outer cover 3 is mainly made of a material having flexibility to prevent damage resulting from friction to tissue in the body cavity.

The inventors of this invention have made extensive research, and as a result, they have found that the use of a material containing polyolefin-based thermoplastic elastomer and polyolefin in a predetermined compounding ratio as a constituent material of the outer cover 3 makes it possible for the outer cover 3 to exhibit especially excellent chemical resistance and heat resistance with retaining adequate resilience, leading to the completion of the present invention.

The amount of polyolefin contained in the constituent material of the outer cover 3 of the flexible insertion tube 1 (that is, a flexible tube for an endoscope of the present invention) is 5 to 70 parts by weight with respect to 100 parts by weight of polyolefin-based thermoplastic elastomer. This makes it possible for the flexible insertion tube 1 to have excellent chemical resistance and heat resistance with retaining adequate resilience. Further, the use of such a material makes it possible for the flexible insertion tube 1 to also improves the abrasion resistance of the flexible insertion tube 1. Furthermore, since polyolefin-based thermoplastic elastomer has excellent miscibility with polyolefin, a more stable outer cover 3 can be obtained.

In this regard, if the amount of the polyolefin to be contained is less than the above lower limit value, the resilience is drastically decreased. Further, abrasion is likely to occur. On the other hand, if the amount of polyolefin to be contained exceeds the above upper limit value, chemical resistance and heat resistance are drastically lowered. Further, since the outer cover 3 becomes hard, it is not possible to obtain a sufficient flexibility.

As described above, the feature of the present invention resides in that the amount of polyolefin to be contained in the constituent material for the outer cover is in the range of 5 to 70 parts by weight with respect to 100 parts by weight of polyolefin-based thermoplastic elastomer, more preferably in the range of 10 to 50 parts by weight, and even more preferably in the range of 20 to 40 parts by weight. By setting the amount of polyolefin to be contained to a value within the above range, the effects described above become more conspicuous.

In this regard, it is to be noted that the compounding ratio of polyolefin with respect to polyolefin-based thermoplastic elastomer may be uniform throughout the outer cover 3, or may be varied continuously or gradually in the thickness direction and/or the longitudinal direction of the outer cover 3.

In this regard, it is to be noted that, besides polyolefin, there are know various polymeric materials having relatively high resilience. However, it is not possible to obtain such an effect as the present invention even if such a polymeric material is used together with polyolefin-based thermoplastic elastomer. For example, as for such a polymeric material, polyester and polystyrene can be mentioned. However, when such a material is used, there arises a problem in that miscibility will be lowered, and therefore chemical resistance and heat resistance are lowered.

Generally, the polyolefin-based elastomer described above is comprised of a hard segment and a soft segment. Examples of a material that can constitute a hard segment include polyethylene, polypropylene and the like. The hard segment may be constituted from one or more of these materials. Further, examples of a material that can constitute a soft segment include vulcanized ethylene-propylene-diene copolymer rubber (EPDM), butyl rubber, chloroprene rubber and the like. The soft segment may be constituted from one or more of these materials.

Examples of polyolefin include polyethylene, polypropylene, and the like, but are not limited thereto. Among these polyolefins, polypropylene is preferable. The use of polypropylene makes it possible to effectively improve heat resistance.

Such polypropylenes can be roughly divided into three types which include homopolypropylene, random polypropylene, and block polypropylene. Among them, homopolypropylene or block polypropylene is particularly preferable. The use of such polypropylene makes it possible for the flexible insertion tube 1 to exhibit more excellent heat resistance.

The average thickness of the outer cover 3 (excluding the portions corresponding to the protruding portions 4) is not limited to any specific value so long as the core member 2 and the elongated members passing through the inside of the core member 2 are protected from fluids such as body fluids and so long as the bendability of the flexible insertion tube 1 is not impaired. Specifically, the average thickness of the outer cover 3 is preferably in the range of about 0.08 to 0.9 mm, more preferably in the range of about 0.1 to 0.8 mm, even more preferably in the range of about 0.3 to 0.6 mm.

Further, the thickness of the outer cover 3 may be varied at different portions along the longitudinal direction thereof, but is preferably substantially uniform. A substantially uniform thickness of the outer cover 3 improves the operability of the flexible insertion tube 1 at the time when the flexible insertion tube 1 is inserted into the body cavity, and thereby a burden placed on a patient can be further reduced.

When necessary, various additives may be added to (contained to) the material of the outer cover 3 (hereinafter also referred to as an "outer cover material"). Examples of the additives include plasticizer; inorganic filler; pigment; various stabilizers (such as antioxidant, photostabilizer, antistatic agent, blocking inhibitor, and lubricant); X-ray contrast medium; and the like.

The flexible insertion tube 1 as described above can be continuously manufactured by, for example, covering the outer periphery of the core member 2 with the outer cover material by means of extrusion molding. Further, by adjusting the discharge quantity (extrusion quantity) of the outer cover material to be extruded through an extrusion opening and the pulling speed of the core member 2, it is possible to control the thickness of the outer cover 3.

Alternatively, the flexible insertion tube 1 may be manufactured in the following manner. For example, the outer cover 3 is formed as a hollow tubular body (tube), and then the core member 2 is inserted into the thus obtained outer cover 3, whereafter, a heating process or the like is carried out to bond the outer cover 3 to the core member 2.

The temperature of the material during extrusion molding is not limited to any specific value, but is preferably in the range of about 130 to 220° C., more preferably in the range of about 165 to 205° C. By setting the temperature of the material during extrusion molding to a value within the above range, the moldability of the outer cover material at the time when the outer cover 3 is formed becomes excellent, and thereby the outer cover 3 can have more uniform thickness.

Next, another embodiment of the flexible insertion tube (flexible tube for an endoscope according to the present invention) will be described.

Figure 3:
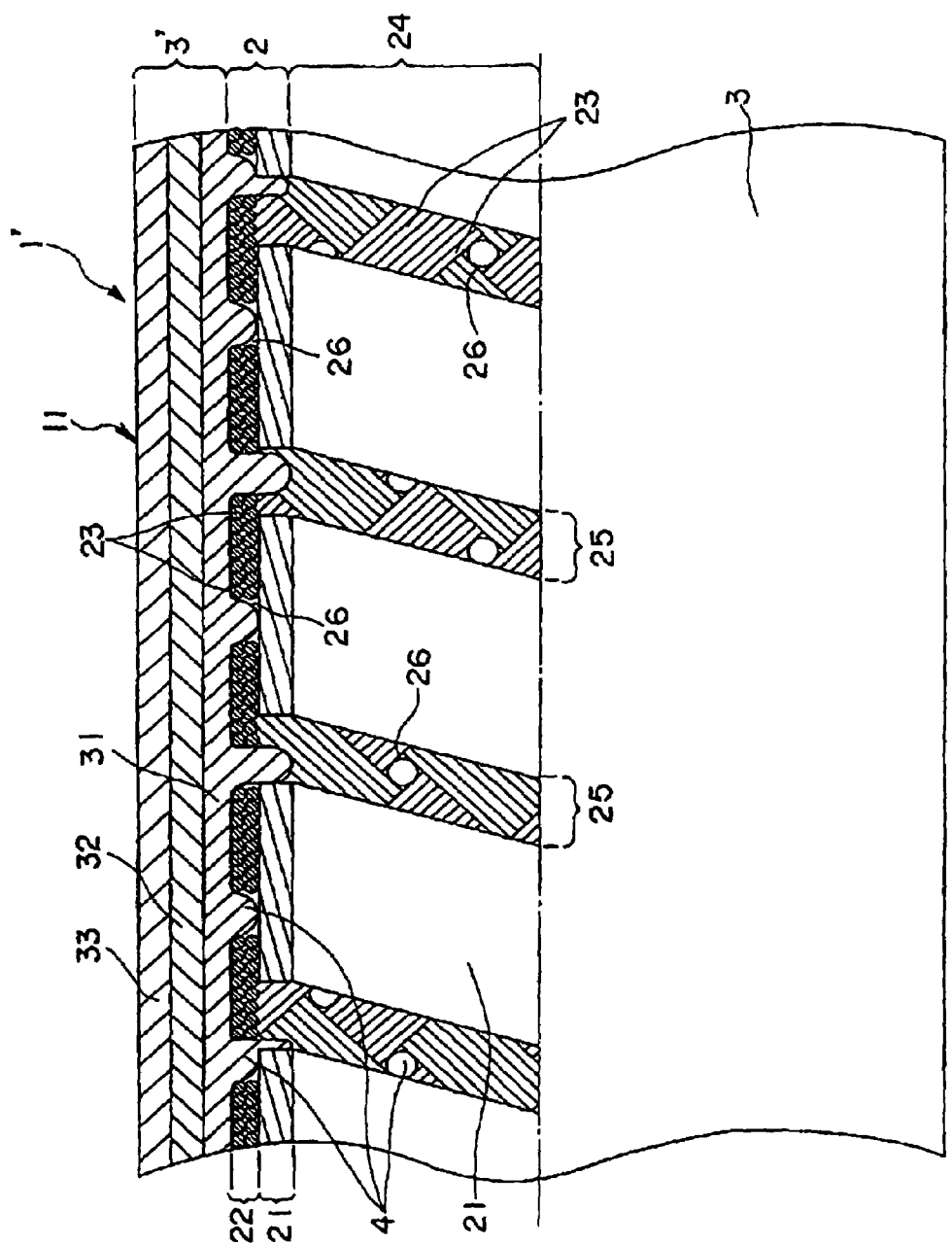
FIG. 3 is an enlarged cross-sectional view of another embodiment of the flexible tube of the endoscope of the present invention.

FIG. 3 is a longitudinal sectional view which shows another embodiment of the flexible insertion tube (flexible tube for an endoscope according to the present invention).

Hereinbelow, a flexible insertion tube 1' shown in FIG. 3 will be described by focusing on elements that are different from those described above for the flexible insertion tube 1, and therefore a description of the same elements will be omitted.

<Flexible Insertion Tube 1'>

The flexible insertion tube 1' is the same as the flexible insertion tube 1 described above except that an outer cover 3' of the flexible insertion tube 1' is formed into a laminated structure which includes an inner layer 31, an intermediate layer 32 and an outer layer 33.

In this embodiment, at least one of the inner layer 31, intermediate layer 32 and the outer layer 33 is made of a material containing polyolefin-based thermoplastic elastomer and polyolefin in a predetermined compounding ratio.

Hereinbelow, a description will be given for the flexible insertion tube 1' in which the outer layer 33 is made of a material containing polyolefin-based thermoplastic elastomer and polyolefin. That is, the structure (material, shape and the like) of the outer layer 33 is the same as that of the outer cover 3 of the embodiment described above.

The average thickness of the outer layer 33 is not limited to any specific value, but is preferably in the range of about 0.01 to 0.6 mm, more preferably in the range of about 0.03 to 0.5 mm. If the thickness of the outer layer 33 is too small, there is a case that sufficient chemical resistance and heat resistance cannot be achieved. On the other hand, if the thickness of the outer layer 33 it too thick, there is a case that the flexible insertion tube 1' is difficult to be freely bent depending on the stiffness of the outer layer 33.

Examples of the constituent material of the inner layer 31 include various resins having flexibility, such as polyvinyl chloride, polyethylene, polypropylene, ethylene-vinylacetate copolymer, polyolefin, polyamide, polyester (e.g., polyethylene terephthalate (PET), polybutylene terephthalate), polyurethane, polystyrene resin, fluorine-based resin (e.g., polytetrafluoroethylene, ethylene-tetrafluoroethylene copolymer), and polyimide; and various elastomers such as polyurethane-based thermoplastic elastomer, polyester-based thermoplastic elastomer, polyolefin-based thermoplastic elastomer, polyamide-based thermoplastic elastomer, polystyrene-based thermoplastic elastomer, fluorine-based thermoplastic elastomer, silicone rubber, fluorine rubber, latex rubber; and the like, but are not limited thereto. These constituent materials can be used singly or in combination of two or more. Among them, polyurethane-based thermoplastic elastomer, polyolefin-based thermoplastic elastomer, or polyester-based thermoplastic elastomer is particularly preferable. The use of such a material makes it possible to control the formation of the protruding portions 4 easily.

The average thickness of the inner layer 31 (excluding those portions corresponding to the protruding portions 4) is not limited to any specific value, but is preferably in the range of about 0.03 to 0.8 mm, more preferably in the range of about 0.03 to 0.4 mm.

The intermediate layer 32 is preferably formed as a layer having better flexibility (resilience) than the outer layer 33. According to this structure, the intermediate layer 32 functions as a cushioning layer between the inner layer 31 and the outer layer 33. Further, it is preferred that the intermediate layer 32 has better flexibility than the inner layer 31 and has excellent adhesion with the outer layer 33.

The cushioning function of the intermediate layer 32 will now be described in detail. When the flexible insertion tube 1' is bent, the deformed intermediate layer 32 generates a strong restoring force because of a high resilience of the intermediate layer 32. Then, since the intermediate layer 32 is arranged between the outer layer 33 and the inner layer 31 both having relatively high hardness, the restoring force of the intermediate layer 32 is transmitted efficiently to the inner layer 31 and the outer layer 33, respectively. As a result, almost all of the restoring force of the intermediate layer 32 functions as a force for restoring the bent flexible insertion tube 1'. Accordingly, by constructing the outer cover 3' to have such a laminated structure described above, it is possible to obtain a flexible insertion tube 1' having excellent resilience.

As for the constituent material of the intermediate layer 32, various resins having flexibility, various elastomers and the like can be mentioned. Among them, low hardness polyurethane-based thermoplastic elastomer, polyolefin-based thermoplastic elastomer, or polyester-based thermoplastic elastomer is particularly preferable. The use of such a thermoplastic elastomer, in particular polyolefin-based thermoplastic elastomer, makes it possible to further improve adhesion between the outer layer 33 and the intermediate layer 32 and to enhance the resilience of the flexible insertion tube 1'. The use of such a thermoplastic elastomer, in particular polyolefin-based thermoplastic elastomer, also makes it possible to further improve adhesion between the outer layer 33 and the intermediate layer 32, thereby enabling to effectively prevent the deterioration of the flexible insertion tube 1', such as peeling-off of the outer layer 33 from the intermediate layer 32, even in a case where the flexible insertion tube 1' is subjected to repeated bandings. Further, by forming the intermediate layer 32 using such a constituent material, it is also possible to improve adhesion between the intermediate layer 32 and the inner layer 31.

The average thickness of the intermediate layer 32 is not limited to any specific value, but is preferably in the range of about 0.02 to 0.8 mm, more preferably in the range of about 0.02 to 0.4 mm.

It should be noted that the laminated structure formed by laminating the plurality of layers described above may be provided for the entire length of the flexible insertion tube 1 in the longitudinal direction thereof or for at least a part of the flexible insertion tube 1 in the longitudinal direction thereof.

As described above, by constructing the outer cover 3' from the outer layer 33 having excellent resilience and having excellent chemical resistance and heat resistance, the intermediate layer 32 having excellent adhesion with the outer layer 33 and excellent resilience, and the inner layer 31 having excellent adhesion with the core member 2, these layers exhibit their respective functions properly. As a result, the outer layer 3' can have especially excellent properties because of a synergistic effect provided by these layers.

This type of flexible insertion tube 1' may be continuously (uniformly) manufactured by covering the outer periphery of the core member 2 with the laminated structure constructed from the inner layer 31, the intermediate layer 32, and the outer layer 33 by the use of an extrusion molding machine equipped with a plurality of extrusion openings. Alternatively, the flexible insertion tube 1' may be manufactured in the following manner. Specifically, each of the layers is formed as a hollow tubular body (tube), and then the core member 2 is inserted into the thus obtained tubular bodies so that the core member 2, the inner layer 31, the intermediate layer 32 and the outer layer 33 may be arranged in this order from the inside to the outside, whereafter a heating process or the like is carried out to bond these elements to each other.

The flexible insertion tube 1' having such a structure and the electronic endoscope 10 equipped with this flexible Insertion tube 1' also have the same effects as those described above.

In this regard, it should be noted that the outer cover 3' is not limited to one having a structure shown in the drawing. For example, the outer cover 3' may be constructed from two layers (e.g., the intermediate layer 32 can be omitted), or the outer cover 3' may be constructed from four or more layers.

Further, although the outer cover 3' having a structure in which a layer made of a constituent material containing polyolefin-based thermoplastic elastomer and polyolefin is arranged on the outermost peripheral side has been described, the layer made of such a constituent material containing polyolefin-based thermoplastic elastomer and polyolefin may be used as an intermediate layer or an innermost layer. Furthermore, two or more layers in the outer cover 3' may be made of such a constituent material containing polyolefin-based thermoplastic elastomer and polyolefin. In this case, the compounding ratio of polyolefin-based thermoplastic elastomer and polyolefin in each of the layers may be the same as to each other or may be varied among these layers.

Although the flexible tube for an endoscope and the endoscope according to the present invention have been described, the present invention is not limited thereto, and so long as the same functions are achieved, it is possible to make various changes or additions to each element (portion) thereof.

In each of the embodiments described above, a flexible Insertion tube has been described as a representative of flexible tubes for endoscopes, but it goes without saying that the flexible tube for an endoscope of the present invention can be applied to flexible connection tubes. Further, although an electronic endoscope (electronic scope) has been described as a representative of endoscopes, it goes without saying that the flexible tube for an endoscope and the endoscope of the present invention can be applied to optical endoscopes (endoscopes of fiber scope type).

Further, in each of the embodiments described above, an endoscope for medical use has been described, but the flexible tube for an endoscope of the present invention can be applied to endoscopes for industrial use.

EXAMPLES

Next, specific embodiments of the present invention will be described.

1. Manufacture of Flexible Tube for an Endoscope

Example 1

First, a spiral coil having an outer diameter of 9 mm and an inner diameter of 7 mm was prepared by winding a band-shaped stainless steel member having a width of 3.2 mm. Then, the spiral coil was jointed at the one end thereof to nodal rings. Next, a plurality of bundles each having ten fine wires made of stainless steel (each of the fine wires had a diameter of 0.08 mm) were prepared, and then these bundles were braided to obtain a reticular tube. The outer periphery of the spiral coil with the nodal rings was covered with this reticular tube to obtain a core member.

Further, polyolefin-based thermoplastic elastomer and polyolefin were prepared. The polyolefin-based thermoplastic elastomer was in the form of a block copolymer which was comprised of a hard segment constituted from polypropylene and a soft segment constituted from ethylene-propylene-diene copolymer, and the polyolefin was homo polypropylene.

Next, these materials are mixed and compounded in a compounding ratio of 5 parts by weight of polyolefin with respect to 100 parts by weight of polyolefin-based thermoplastic elastomer. Then, the outer periphery of the core member was covered with an outer cover made of the compounded materials by using the extrusion molding method so that the thickness of the outer cover might be 0.4 mm, to obtain a flexible tube for an endoscope with a length of 1.5 m.

Examples 2 to 5

In each of these Examples, a flexible tube for an endoscope was manufactured in the same manner as in Example 1 except that the compounding ratio of polyolefin-based thermoplastic elastomer and polyolefin was changed into each ratio shown in Table 1.

Example 6

A flexible tube for an endoscope was manufactured in the same manner as in Example 1 except that an outer cover was formed into a laminated structure including an outer layer, an intermediate layer and an inner layer, in which the outer layer was formed of a constituent material containing 5 parts by weight of polyolefin and 100 parts by weight of polyolefin-based thermoplastic elastomer.

The laminated structure was manufactured using an extrusion molding machine equipped with three extrusion openings. Namely, the outer cover having a laminate structure was continuously manufactured by extruding the materials of the inner layer, the intermediate layer and the outer layer simultaneously so as to cover the core member.

As for the constituent materials of each of the inner and intermediate layers, polyurethane-based thermoplastic elastomer (manufactured and sold by DIC Bayer Polymer Ltd. with the product name of "PANDEX"), and polyolefin-based thermoplastic elastomer (manufactured and sold by Mitsubishi Chemical Corporation with the product name of "THERMORUN") were used, respectively.

Further, the thickness of each of the inner, intermediate and outer layers were 0.15 mm, 0.1 mm and 0.3 mm, respectively.

Examples 7 to 10

In each of these Examples, a flexible tube for an endoscope was manufactured in the same manner as in Example 6 except that the compounding ratio of polyolefin-based thermoplastic elastomer and polyolefin was changed Into each ratio shown in Table 1.

Comparative Example 1

A flexible tube for an endoscope was manufactured in the same manner as in Example 1 except that the constituent material of the outer cover was changed to polyurethane-based thermoplastic elastomer (manufactured and sold by DIC Bayer Polymer Ltd. with the product name of "PANDEX").

Comparative Example 2

A flexible tube for an endoscope was manufactured in the same manner as in Example 1 except that the constituent material of the outer layer was changed to a material containing no polyolefin.

Comparative Examples 3 and 4

In each of the Comparative Examples, a flexible tube for an endoscope was manufactured in the same manner as in Example 1 except that the compounding ratio of polyolefin-based thermoplastic elastomer and polyolefin was changed as shown in Table 1.

Comparative Example 5

A flexible tube for an endoscope was manufactured in the same manner as in Example 6 except that the constituent material of the outer layer was changed to polyurethane-based thermoplastic elastomer (manufactured and sold by DIC Bayer Polymer Ltd. with the product name of "PANDEX").

Comparative Example 6

A flexible tube for an endoscope was manufactured in the same manner as in Example 6 except that the constituent material of the outer layer was changed to a material containing no polyolefin.

Comparative Examples 7 and 8

In each of the Comparative Examples, a flexible tube for an endoscope was manufactured in the same manner as in Example 6 except that the compounding ratio of polyolefin-based thermoplastic elastomer and polyolefin was changed as shown in Table 1.

The constituent material and the average thickness of the outer cover of each of Examples and Comparative Examples are shown in Table 1 (it should be noted that, in the case of each of Examples 6 to 10, the constituent material and the average thickness of the outer layer thereof are shown).

Further, it should be noted that in the Table 1 polyolefin-based thermoplastic elastomer, polyolefin, polyurethane-based thermoplastic elastomer are abbreviated as "TPO", "PO" and "TPU", respectively.

TABLE 1

|  | Constituent material of outer cover | Average thickness (mm) |
| --- | --- | --- |
| Example 1 | TPO: 100 parts by weight<br>PO: 5 parts by weight | 0.4 |
| Example 2 | TPO: 100 parts by weight<br>PO: 10 parts by weight | 0.4 |
| Example 3 | TPO: 100 parts by weight<br>PO: 30 parts by weight | 0.4 |
| Example 4 | TPO: 100 parts by weight<br>PO: 50 parts by weight | 0.4 |
| Example 5 | TPO: 100 parts by weight<br>PO: 70 parts by weight | 0.4 |
| Example 6 | TPO: 100 parts by weight<br>PO: 5 parts by weight | 0.3 |
| Example 7 | TPO: 100 parts by weight<br>PO: 10 parts by weight | 0.3 |
| Example 8 | TPO: 100 parts by weight<br>PO: 30 parts by weight | 0.3 |
| Example 9 | TPO: 100 parts by weight<br>PO: 50 parts by weight | 0.3 |
| Example 10 | TPO: 100 parts by weight<br>PO: 70 parts by weight | 0.3 |
| Comp. Ex. 1 | TPU | 0.4 |
| Comp. Ex. 2 | TPO | 0.4 |
| Comp. Ex. 3 | TPO: 100 parts by weight<br>PO: 2 parts by weight | 0.4 |
| Comp. Ex. 4 | TPO: 100 parts by weight<br>PO: 90 parts by weight | 0.4 |
| Comp. Ex. 5 | TPU | 0.3 |
| Comp. Ex. 6 | TPO | 0.3 |
| Comp. Ex. 7 | TPO: 100 parts by weight<br>PO: 2 parts by weight | 0.3 |
| Comp. Ex. 8 | TPO: 100 parts by weight<br>PO: 90 parts by weight | 0.3 |

2. Evaluation of Properties of Flexible Tube for an Endoscope 2.1 Chemical Resistance Test Chemical resistance test was carried out on the flexible tube for an endoscope manufactured in each of Examples and Comparative Examples in the following manner.

In this chemical resistance test, each of the flexible tubes for endoscopes was subjected to a cleaning and disinfection operation by the use of a heating-type cleaner (manufactured and sold by BHT Corp. with the product name of "SME 2000").

This cleaning and disinfection operation was carried out through four processes, i.e., a cleaning process using a cleaning solution (nonionic surfactant) (about 10 minutes), a disinfection process using a disinfectant solution (about 0.24 wt % aqueous glutaraldehyde solution) (about 10 minutes), a washing process using hot water at about 60° C. (about 10 minutes), and a drying process with hot air (about 5 minutes).

After this cleaning and disinfection operation was repeated 2,000 times, the appearance of the flexible tube for an endoscope was observed, and was then evaluated according to the following four criteria.

A: No change in appearance
B: Almost no loss of luster and yellowing
C: Slight loss of luster and yellowing
D: Noticeable loss of luster and yellowing 2.2 Heat Resistance Test Heat resistance test was carried out on the flexible tube for an endoscope manufactured in each of Examples and Comparative Examples in the following manner.

Three flexible tubes for endoscopes were prepared for each of Examples and Comparative Examples. Each of the flexible tubes for endoscopes was subjected to autoclave sterilization for 15 minutes at a temperature of 135° C. and under a pressure of 2.2 atmospheres, and was then rapidly cooled in ice water. This series of operations was repeated 20 times.

After the series of operations was repeated 20 times, the degree of deterioration of each of the flexible tubes for endoscopes, especially the degree of loss (lowering) of flexibility was examined, and was then evaluated according to the following four criteria.

A: Almost no change in flexibility
B: Slight loss of flexibility
C: Noticeable loss of flexibility
D: Stiff state (significant deterioration)

2.3 Resilience Test

Resilience test was carried out on the flexible tube for an endoscope manufactured in each of Examples and Comparative Examples in the following manner.

In this resilience test, ten flexible tubes for endoscopes were prepared for each of Examples and Comparative Examples, and then these ten flexible tubes for endoscopes were tied in a bundle to examine whether or not this bundle could be bent.

After such bending operation was carried out, the resilience of each of the flexible tubes for endoscopes was evaluated according to the following four criteria.

A: Extremely good resilience
B: Good resilience
C: Poor resilience
D: Virtually no resilience (stiff state)

The results of these evaluations are shown in Table 2.

TABLE 2

|  | Chemical Resistance | Heat resistance | Resilience |
| --- | --- | --- | --- |
| Example 1 | A | A | C |
| Example 2 | A | A | B |
| Example 3 | A | A | A |
| Example 4 | A | A | B |
| Example 5 | A | A | C |
| Example 6 | A | A | B |
| Example 7 | A | A | A |
| Example 8 | A | A | A |
| Example 9 | A | A | A |
| Example 10 | A | A | B |
| Comp. Ex. 1 | D | D | A |
| Comp. Ex. 2 | A | A | D |
| Comp. Ex. 3 | A | A | D |
| Comp. Ex. 4 | A | A | D |
| Comp. Ex. 5 | D | D | A |
| Comp. Ex. 6 | A | A | D |
| Comp. Ex. 7 | A | A | D |
| Comp. Ex. 8 | A | A | D |

As is apparent from Table 2, all of the flexible tubes for endoscopes of the present invention had excellent chemical resistance and heat resistance with retaining adequate resilience.

On the other hand, the flexible tubes for endoscopes of Comparative Examples were inferior in performance to those of Examples.

Effects of the Invention

As has been described above, according to the present invention, it is possible to obtain a flexible tube for an endoscope having excellent chemical resistance and heat resistance with retaining resilience.

In particular, in a case where the outer cover is formed into a laminated structure constructed from a plurality of layers, these layers exhibit their respective functions so that the flexible tube for an endoscope can have especially excellent properties due to a synergistic effect among the layers.

Finally, it is to be understood that many changes and additions may be made to the embodiments described above without departing from the scope and spirit of the invention as defined in the following claims.

Further, it is also to be understood that the present disclosure relates to subject matter contained in Japanese Patent Application No. 2003-188088 (filed on Jun. 30, 2003 which is expressly incorporated herein by reference in its entirety.

What is claimed is:

1. A flexible tube for an endoscope, comprising:
    a tubular core member; and
    an outer cover provided around the core member, the outer cover being formed of a material containing as a major component thereof polyolefin-based thermoplastic elastomer and polyolefin, wherein the amount of the polyolefin contained in the material is 5 to 70 parts by weight with respect to 100 parts by weight of the polyolefin-based thermoplastic elastomer.

2. The flexible tube for an endoscope as claimed in claim 1, wherein the outer cover has a laminated structure including a plurality of layers, wherein at least one of the layers is formed of the material containing polyolefin-based thermoplastic elastomer and polyolefin.

3. The flexible tube for an endoscope as claimed in claim 2, wherein the layer formed of the material containing polyolefin-based thermoplastic elastomer and polyolefin is an outermost layer among the plurality of layers.

4. The flexible tube for an endoscope as claimed in claim 2, wherein the average thickness of the layer formed of the material containing polyolefin-based thermoplastic elastomer and polyolefin is in the range of 0.01 to 0.6mm.

5. The flexible tube for an endoscope as claimed in claim 1, wherein the polyolefin is mainly constituted from polypropylene.

6. The flexible tube for an endoscope as claimed in claim 1, wherein the average thickness of the outer cover is in the range of 0.08 to 0.9mm.

7. An endoscope equipped with the flexible tube defined in claim 1.

8. An endoscope equipped with the flexible tube defined in claim 2.

9. An endoscope equipped with the flexible tube defined in claim 3.

10. An endoscope equipped with the flexible tube defined in claim 4.

11. An endoscope equipped with the flexible tube defined in claim 5.

12. An endoscope equipped with the flexible tube defined in claim 6.

13. The flexible tube for an endoscope as claimed in claim 1, wherein the amount of the polyolefin contained in the material is 20 to 40 parts by weight with respect to 100 parts by weight of the polyolefin-based thermoplastic elastomer.

14. The flexible tube for an endoscope as claimed in claim 1, wherein the polypropylene is homopolypropylene.

* * * * *